United States Patent
Dessing

(10) Patent No.: US 12,284,978 B2
(45) Date of Patent: Apr. 29, 2025

(54) MILKING SYSTEM WITH DETECTION SYSTEM

(71) Applicant: LELY PATENT N.V., Maassluis (NL)

(72) Inventor: Jacobus Petrus Maria Dessing, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 990 days.

(21) Appl. No.: 17/273,966

(22) PCT Filed: Sep. 19, 2019

(86) PCT No.: PCT/NL2019/050622
§ 371 (c)(1),
(2) Date: Mar. 5, 2021

(87) PCT Pub. No.: WO2020/067884
PCT Pub. Date: Apr. 2, 2020

(65) Prior Publication Data
US 2021/0259194 A1    Aug. 26, 2021

(30) Foreign Application Priority Data

Sep. 24, 2018 (NL) ...................................... 2021688
Jan. 31, 2019 (NL) ...................................... 2022489

(51) Int. Cl.
*A01J 5/013* (2006.01)
*G01N 1/31* (2006.01)
(Continued)

(52) U.S. Cl.
CPC ........... *A01J 5/0131* (2013.01); *A01J 5/0135* (2013.01); *G01N 1/312* (2013.01); *G01N 33/04* (2013.01);
(Continued)

(58) Field of Classification Search
CPC ...... A01J 5/0131; A01J 5/0135; G01N 1/312; G01N 33/04; G01N 35/00009;
(Continued)

(56) References Cited

U.S. PATENT DOCUMENTS

| | | | |
|---|---|---|---|
| 5,096,828 A * | 3/1992 | Ishizaka | G01N 35/00009 422/66 |
| 5,370,842 A | 12/1994 | Miyazaki et al. | |
| 2002/0124803 A1* | 9/2002 | Chen | A01K 1/12 119/14.08 |

FOREIGN PATENT DOCUMENTS

| | | |
|---|---|---|
| CA | 3 045 602 A1 | 6/2018 |
| CN | 103796509 A | 5/2014 |

(Continued)

OTHER PUBLICATIONS

Fu, "Food Safety Detection Technology," University of Electronic Science and Technology of China Press, ISBN: 978-7-5647-3772-6, 2016, 18 pages, with English abstract.
(Continued)

*Primary Examiner* — Jill A Warden
*Assistant Examiner* — Alex Ramirez
(74) *Attorney, Agent, or Firm* — Birch, Stewart, Kolasch & Birch, LLP

(57) ABSTRACT

A milking system with a milking device, a milk line, and a sampling and analysis device to sample and analyse the milk are disclosed. The sampling and analysis device includes a control unit, a tape wound on a tape reel, and including a base material with a series of reagent pads arranged to provide a detectable response in the presence of a substance in the sample, a tape mover to move and unwind the tape, a dosing device to provide a part of the sample onto one of the reagent pads, and an optical sensor device to detect optical radiation from said reagent pad with said sample, and to analyse the detected optical radiation to provide an indica-
(Continued)

Figure 1:
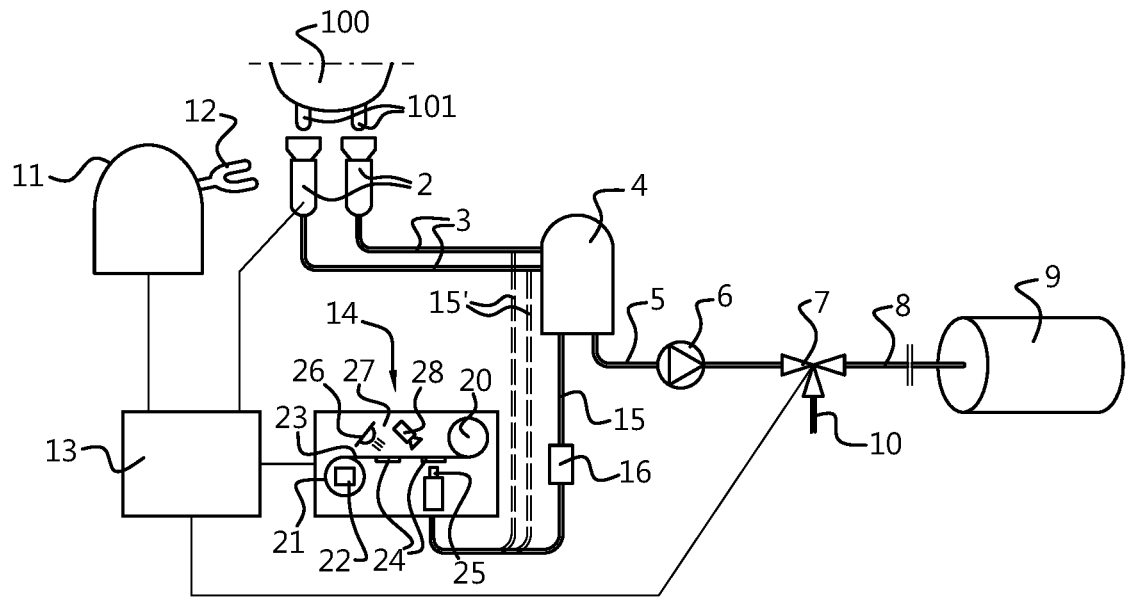

tion of a presence or concentration of said substance. The dosing device includes a displaceable nozzle with a supply line for supplying the sample to the nozzle. The nozzle is arranged for supplying the sample upwardly to the reagent pad. The dosing device further includes a nozzle mover to move the displaceable nozzle towards and away from the tape, and an overflow device, or cup, including a wall that surrounds the nozzle. An overflow space is provided between the wall and the nozzle, and further includes a discharge. The overflow device can collect excess fluid, both when sampling and certainly when flushing. Herein, gravity helps in collecting fluid, but importantly, also in supplying the sample, since the sample droplet cannot break off the nozzle unexpectedly.

12 Claims, 1 Drawing Sheet

(51) Int. Cl.
*G01N 33/04* (2006.01)
*G01N 35/00* (2006.01)

(52) U.S. Cl.
CPC . *G01N 35/00009* (2013.01); *G01N 2001/317* (2013.01); *G01N 2035/00039* (2013.01); *G01N 2035/00148* (2013.01)

(58) Field of Classification Search
CPC ... G01N 2001/317; G01N 2035/00039; G01N 2035/00148
See application file for complete search history.

(56) References Cited

FOREIGN PATENT DOCUMENTS

| CN | 107703078 A | 2/2018 |
| WO | WO 02/069697 A1 | 9/2002 |
| WO | WO 2004/034063 A2 | 4/2004 |
| WO | WO 2004/081436 A1 | 7/2004 |
| WO | WO 2008/126827 A1 | 10/2008 |

OTHER PUBLICATIONS

International Search Report, issued in PCT/NL2019/050622, dated Feb. 19, 2020.
Written Opinion of the International Searching Authority, issued in PCT/NL2019/050622, dated Feb. 19, 2020.

* cited by examiner

MILKING SYSTEM WITH DETECTION SYSTEM

The present invention relates to a milking system with a milking device for milking milk from a dairy animal, a milk line in fluid connection with the milking device, and a sampling and analysis device being arranged to take a sample of the milk from the milk line and to analyse milk from the sample, the sampling and analysis device comprising a control unit for controlling the sampling and analysis device, a tape wound on a tape reel carrying the tape, said tape comprising a base material with provided thereon a series of reagent pads, that are arranged to provide a detectable response in the presence of at least one substance in the sample, a tape mover, arranged to move and unwind the tape under the control of the control device, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance.

Document WO02069697A1 discloses a sampling and analysis device in a milking system, with a tape carrying test strips or dry sticks with reagents, and a valve fior dosing a few drops of milk onto the test strips. A funnel beneath the tape receives excess milk via flushing holes in the tape.

A problem with known devices is that it may prove difficult to keep the sampling and analysis device clean during all circumstances. Therefore, the reliability and accuracy of the measurements may not always be guaranteed.

It is therefore an object of the present invention to provide a milking system of the kind mentioned above, which can be kept clean more easily, which shows reliable and accurate measurements, and/or which achieves (excess) liquid control by means of simple measures.

The present invention achieves this at least in part by means of a milking system according to claim, in particular a milking system with a milking device for milking milk from a dairy animal, a milk line in fluid connection with the milking device, and a sampling and analysis device being arranged to take a sample of the milk from the milk line and to analyse milk from the sample, the sampling and analysis device comprising a control unit for controlling the sampling and analysis device, a tape wound on a tape reel carrying the tape, said tape comprising a base material with provided thereon a series of reagent pads, that are arranged to provide a detectable response in the presence of at least one substance in the sample, a tape mover, arranged to move and unwind the tape under the control of the control device, a dosing device arranged to provide, under the control of the control unit, a part of the sample onto one of the reagent pads, an optical sensor device arranged to detect optical radiation from said reagent pad supplied with said part of the sample, and to analyse the detected optical radiation to provide an indication of a presence or concentration of said at least one substance, wherein the dosing device comprises a displaceable nozzle with a supply line for supplying a portion of the milk sample to the nozzle, the nozzle being arranged for supplying the part of the sample upwardly to the reagent pad, wherein the dosing device further comprises a nozzle mover that is arranged to move the displaceable nozzle towards and away from the tape under the control of the control unit, wherein the dosing device comprises an overflow device that is arranged to collect excess fluid supplied by the nozzle and that comprises a wall, in particular a cup, the wall at least partly surrounding the nozzle, an overflow space being provided between the wall and the nozzle, further comprising a discharge connected or connectable to the overflow space.

The present invention is based on the insight that gravity may help in the control of liquid, by actually counteracting the intended flow instead of increasing the intended flow. It furthermore ensures that excess liquid will be returned to its origin, instead of ending up in the system uncontrolled. This allows better control over the removal of excess liquid, either directly, i.e. before reaching the tape, or after supplying to the tape, in that excess liquid drops off, back towards the nozzle with the surrounding overflow device. Thereby less remnants may cause soiling or disturb measurements. It also allows to do away with any flushing holes in the tape with reagents. Thereby, the reagents may be brought closer together, so that more reagent pads may be provided on the tape. This in turn ensures a longer uninterrupted operation of the device with a given length of tape.

In the present invention, thereto, the nozzle is arranged to provide the sample droplet(s) upwardly, and furthermore is surrounded by an overflow device, that serves to catch excess liquid, both flowing from the nozzle itself directly, or from the reagent pads or tape after sample delivery. In other word, gravity, which pulls downward, counteracts the supplying of a sample droplet, which occurs upward. In addition to the effects mentioned above, this also achieves better control over supplying of the sample droplet, that cannot now suddenly free itself from the nozzle under the influence of a pulling gravity, but instead must be actively ejected.

Furthermore, providing on the one hand the nozzle such that gravity pulls liquid away from the tape, and on the other hand an overflow device achieves the advantage that cleaning the nozzle, and the corresponding parts of the sample line, is now easier. After all, supplying cleaning fluid to the nozzle need not provide any such liquid onto the tape with the reagents, since all this liquid may be pulled away towards the overflow device, in contrast with the known device, where all liquid must pass the tape.

The overflow device comprises a wall that at least partly surrounds the nozzle, and a discharge for draining off the excess fluid. This discharge may be closable, and in this way connectible to the overflow device. The wall may have any suitable shape, even flat, as long as the excess fluid will be drained off effectively. The latter could be achieved by means of a vacuum, that actively sucks away any liquid falling onto the wall.

It will however be advantageous if liquid falling onto the wall is kept from falling off the wall. Thereto, the wall is preferably a cup, meaning that there is at least a circular erect wall part to contain collected fluid until drained off.

Particular embodiments, features and advantages are described in dependent claims and in the now following part of the description.

It may suffice in some embodiments if the sample causes a chemical reaction in the reagent pad that emits optical radiation. In such case, an optical radiation source is not required. In most cases, and in corresponding embodiments, it is advantageous to have an optical radiation source that is controlled by the control unit. This allows a good control over the optical radiation emitted onto the reagent pads, and thus also ensures a good accuracy when determining the presence or concentration of a substance based on optical properties of the reagent pad supplied with the sample. Such optical radiation sources may be one or more LEDs, (halogen) incandescent light bulbs, lasers and so on. These may be readily selected by the skilled person.

In embodiments, the milking system, in particular the sampling and analysis system, further comprises a dosing control device comprising a wall part for closing off the nozzle upon contact, and a mover arranged to position the wall part between the nozzle and the tape, preferably to press the wall part and the nozzle onto one another. This allows to clean in particular the nozzle with more force, i.e. with a liquid flow with a higher speed. Herein, the wall part serves to shield off any jets or droplets of liquid that could otherwise be forcefully ejected towards the tape, which is undesirable. By furthermore pressing the wall part and the nozzle onto one another, the cleaning liquid may be kept from squirting around, and be collected in the overflow device effectively.

The wall part may have any shape that is useful in achieving the abovementioned goal. For example, the wall part may be concave with respect to the nozzle, which helps in catching liquid ejected from the nozzle. In particular embodiments, the wall part is a flat wall part. Such a wall part may contact the nozzle reliably without any additional positioning measures. Furthermore, and importantly, it allows to define a precise filling level of the nozzle, in particular up to the rim of the nozzle. This in turn allows a very accurate dosing of liquid, in casu milk, because it is then exactly known how much the liquid body in the line to the nozzle, which line is now completely filled with liquid right up to the nozzle, must be moved forward by some pump means. Although it is still possible to have a different wall part shape, such as concave or convex, this makes the control more difficult, not only because the exact shape at the nozzle is less well-defined, but in addition because then additional measures should be provided to ensure that the nozzle and the wall part contact each other in the same, or at least a known place, which is not relevant in case of a flat wall part.

It is noted that the mover is arranged to position the wall part between the nozzle and the tape, preferably to press the wall part and the nozzle onto one another. This may be achieved by having the mover move the nozzle toward a fixed wall part, by having the mover move the wall part toward the nozzle, or by having the mover move both the wall part and the nozzle, toward each other. The last option is preferred, in that the mover moves to wall part to a position between the tape and the nozzle, and then moves the nozzle toward the wall part. In that way, the nozzle only need move in a longitudinal direction, which movement is also useful when delivering the sample drop to the reagent pad, after which delivery it is preferable to retract the nozzle away from the tape.

In embodiments, the wall part comprises a flexible material, in particular an elastic membrane. By means of the flexible material, tolerances in the nozzle surface may be accounted for, such that the contact is achieved for substantially every nozzle surface. This also allows excess liquid to escape more easily between nozzle surface and the wall part. In addition, because the wall part is flexible, the counter-force exerted on the liquid is relatively small, and well-defined. All this further helps in the formation of a well-defined meniscus. Herein, "flexible" means that the wall part may undergo a detectable elastic deformation under the influence of the pressure of the liquid from the nozzle. The wall part is preferably an elastic membrane, such as in particular a rubber membrane. Naturally, the wall part will preferably be a flat wall part, in particular since that is the natural shape of a pretensioned elastic membrane.

In embodiments, the milking system, in particular the sampling and analysis system, further comprises a sealing rim arranged around the wall part, the sealing rim and the wall part together forming a second space for receiving the nozzle. In this way, the rim prevents liquid that is ejected between the nozzle and the wall part from being hurled into the environment of the nozzle. Rather, the rim causes the liquid to be collected in the second space, and thus remain close to the nozzle. Thereby, it may be collected effectively by the overflow device.

In embodiments, the wall of the overflow device and the sealing rim are in sealing contact when the nozzle is received in the second space, the overflow space and the second space being in direct fluid connection. This feature ensures that there is a closed-off space for collecting fluid from the nozzle, from which the fluid may be drained directly. This in turn allows for higher speeds of the liquid, which is advantageous when cleaning the nozzle.

Preferably, the discharge has a cross-sectional discharge area that is at least twice as large as a cross-sectional supply area of the supply line. This ensures that the discharge of the collected liquid/excess liquid is substantially always possible with a low pressure/low vacuum, which helps in preventing draining problems, as well as prevents counter-pressure on the liquid in the nozzle.

Figure 2:
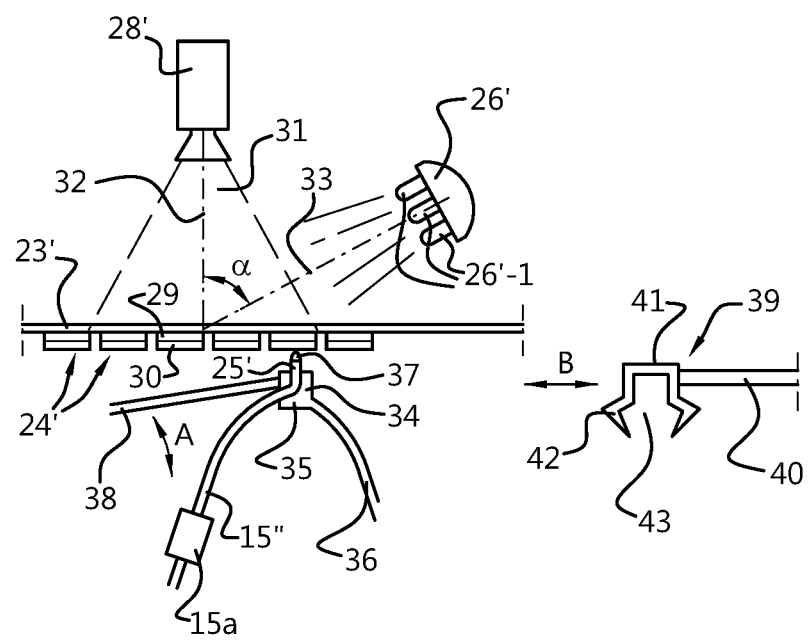

The invention will now be elucidated by way of a number of exemplary embodiments and the drawings, in which FIG. 1 shows a diagrammatic representation of a milking system according to the present invention; and FIG. 2 diagrammatically shows a partly cross-sectional view through a part of an embodiment of the invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. The sampling unit 14 comprises a supply reel 20 and a collecting reel 21 that is driven by a tape mover 22, for positioning a tape 23 with reagent pads 24. A nozzle device for sample droplets is denoted by 25, a light source 26 emits light 27, and a camera is denoted by 28.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be of good quality, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 16. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on. It is remarked that in robotic milking systems animal identification systems are present, so that animal ID during milking is known. Thereby, any measurement result will be coupled to the corresponding animal file in a database system.

Furthermore, a sampling unit 14 is very generally shown here, in that it contains a supply reel 20 and a collecting reel 21, between which a tape 23 is advanced by means of tape mover means 22, such as a cassette deck motor or stepper motor. The tape 23 carries reagent pads 24 that contain reagent that gives a detectable response in the presence of a defined substance, often the intensity of the response depending on the concentration of the substance brought into the reagent via the sample droplet. Such a sample droplet is delivered via the nozzle 25. A light source 26 then shines light 27 onto the reagent pad 24, and a camera 28 observes the response, if any, in the reagent pad. The light source 26 may be any suitable light source, such as one or more LEDs, and the emitted light 27 may be visible light, UV (A) radiation, (near) infrared, and so on, depending on the used reagent. Of course, the camera 28 should be adapted to detect radiation coming from the reagent pad 24. Often, this is reflected or scattered light, but it could be different radiation, such as fluorescence radiation. In any case, details of such radiation and detection may easily be implemented by the skilled person and do not form the present invention as such.

In the embodiment shown, the sample droplet is supplied to the reagent pad 24 in a way of which the details will be provided in relation with FIG. 2.

FIG. 2 diagrammatically shows a partly cross-sectional view through a part of an embodiment of the invention. Herein, similar parts are given the same reference numerals, sometimes with a single or double prime ("/").

Here, the tape 23' is provided with a series of reagent pads 24' that have a bottom layer 29 and a top layer 30. The nozzle 25' is connected to the sample line 15" with a sample pump 15a, the nozzle providing a sample droplet 37, and being provided in, and surrounded by, an overflow cup 34, which has an overflow space 35 with a drain 36 and is connected to a nozzle mover arm 38 that is moveable in the direction of the double arrow A. A rinsing cup 39 is moveable by means of a connected rinsing cup moving arm 40 in the direction of the double arrow B, and comprises a bottom 41 and a bellows 42, and surrounds a rinsing space 43. The camera 28' has a field-of-view 31 with a line of main direction 32. The light source 26' comprises three LEDs 26'-1 and shines in a solid angle with a line of main direction 33, that makes an angle a with line 32.

In a typical operation of the system, first the nozzle 25' can be rinsed with fluid, to remove residues from previous sampling and/or to bring the nozzle to a desired temperature, by rinsing with correspondingly heated fluid. This may be done by supplying liquid via the sample pump 15a through the sample line 15", and collecting the liquid emerging from the nozzle 25' in the overflow cup 34 by means of gravity. The collected fluid is drained via the drain 36.

However, it is advantageous if the liquid for rinsing is supplied more vigorously. This can be achieved by moving the nozzle somewhat away from the tape 23' by operating the nozzle mover arm 38 by any suitable means such as pneumatics or an electromotor, and moving the rinsing cup 39 between the nozzle and the tape by operating the rinsing cup moving arm by, again, any suitable means such as an electromotor, followed by inserting the nozzle into the rinsing space 43. In practice this will come down to inserting the nozzle 25' together with the overflow cup 34 into the rinsing space 43. However, if no overflow cup is provided, it is also possible to arrange the rinsing cup with such dimensions that it seals off the nozzle. A drain should then be provided in the rinsing cup 39. Note that it is not necessary to seal off the nozzle 25', with the overflow cup 34, by means of the rinsing cup 39. It may in fact suffice if the tip of the nozzle 25' is surrounded by the rinsing cup 39, and that the overflow cup 34 is wider than the rinsing cup 39. In that case any fluid ejected by the nozzle will then either flow down along the nozzle into the overflow cup, or it will be ejected more forcefully but then be stopped by the rinsing cup 39, after which it will drip down into the overflow cup 34. Nevertheless, it is advantageous if the nozzle cum overflow cup 34 is actually sealed off by the rinsing cup because then excess evaporation of liquid used in the process of rinsing etc. will be prevented. This is desirable in particular in the case of moisture sensitive reagents as often used in biosensing, such as in the present case of milk sampling. Thus preferably, when inserted, the nozzle 25' with the overflow cup 34 is sealed by the bellows 42 of the rinsing cup 39. Thereby, the overflow space 35 and the rinsing space 43 form a single sealed off space. Now, rinsing fluid may be supplied to the nozzle 25' with vigour, such as with 2 m/s. The liquid will then be ejected from the nozzle but will not escape the overflow space/rinsing space 35/43. From there, the fluid will be drained by means of the drain 36. Finally, it will be ensured that the nozzle is completely filled with sample liquid, in particular milk, by pressing the nozzle 15" in direct contact with the bottom 41, being a flat part, of the rinsing cup 39, and subsequently eject more liquid. The bottom 41 is somewhat elastic, and this ensures that there will be a clearly defined meniscus of sample liquid in the now completely filled, and air bubble-less nozzle. The nozzle arm 38 will then move the nozzle downward, out of the rinsing cup 39, and the rinsing cup moving arm 40 will move the rinsing cup 39 to the side, to clear the way for the nozzle to reach the reagent pads.

Next, a dosing pump, in particular the sample pump 15a, such as a peristaltic pump, may dose a known amount of sample fluid, to form the sample droplet 37 of now known dimensions. This helps in preventing excess fluid that may drop off unexpectedly, and also ensures that it will be known when the droplet 37 will touch the reagent pad 24". The nozzle mover arm 38 will then move upward again to bring the droplet 37 to a reagent pad 24', where a reaction and response may be brought about.

This reaction can be observed by the camera 28', that looks straight down through the tape, with a field-of-view 31 with a central line 32. This allows the camera 28' to observe the reaction in the reagent pad 24' from the opposite side with respect to the sample liquid supplied in the droplet 37. This prevents that already coloured reagent material blocks the observation of further response in fresh reagent material, or that not yet absorbed sample liquid blocks the view altogether. This is particularly helpful in double layer reagent pads such as shown in the figure. Sometimes it takes a two-step reaction, such as in the case of flow-through tests. Herein, the present set-up with the double layer may provide an alternative to these flow-through tests or also lateral flow tests. Since these take more time, it is then advantageous when more than one reagent pad 24' is in the field-of-view 31, since the tape and thus each pad 24' is advanced one pad length for every sampling, such as for every milking. Since the latter may be as short as five minutes, it is advantageous to allow more pads in the view of the camera 28' to allow more time for observing the response. It is remarked that even with single layer reagent pads 24', having more pads in view of the camera is useful, since then the concentration of the reagent in the pad 24' may be less than would be needed if the response would have to be assessed in those five minutes.

It is remarked that the camera 28' need not itself be positioned (directly or not) above the tape 23', as long as the optical path (the "view") of the camera 28' is on the other side of the tape 23' as where the reagent pads 24' are. In other words, the camera should look through the tape. The physical position of the camera 28' may be changed e.g. by using mirrors or the like. These may e.g. be used to fold up the optical path, and make the analyser device more compact.

The light source 26' used in the present embodiment comprises three LEDs 26'-1. These can be white light LEDs that together shine a homogeneous but bright light, in a main direction 33 that makes a sharp angle a with the line 32 of the camera's field-of-view, in order to prevent blurring or glaring of the camera image. The light source may also comprise other types, such as a combination of red, green and blue LEDs, halogen incandescent and so on. The light emitted may be visible light, near infrared, ultraviolet (UVA) or the like. The tape 23' should of course be transparent for the light used.

In use of the system, the droplet 37 is provided from below. This means that gravity in principle pulls back the droplet into the nozzle 25', instead of pulling it out of said nozzle. This helps in controlling the forming and the ejection of the droplet 37. It cannot suddenly drop off from the nozzle, due to some vibration or even mere coincidence. This ensures that the droplet cannot fall from the nozzle onto the camera 28', that images the reagent pads 24'. Even if there would be excess liquid supplied to the reagent pad 24', such liquid would not fall onto the camera, or on an optional window provided between the camera and the tape with the reagent pads. In this way, the camera 28' will always have a clear picture of the reagent pads, even without such a window. In the Figure, the camera is tilted slightly to the left. The tilting of the optical path may also be brought about by means of a mirror or the like.

Having the sample drop supplied from below also allows an improved control over supplying of the droplet in that excess liquid may now easily be sucked off the reagent pad. Again, gravity helps, by preventing breaking off of the droplet from the nozzle, such that in principle there will remain a connection between the droplet, even when contacting the reagent pad, and the nozzle. In case the connection would be broken after all, that is a clear indication that substantially all liquid has been absorbed by the reagent pad, and thus there will neither be a problem with liquid lateron falling off unexpectedly. Obviously, the type of sample pump or dosing pump 15a should allow such sucking back, e.g. a peristaltic pump with a reversible pump drive.

The above described embodiments only serve to help explain the invention without limiting this in any way. The scope of the invention is rather determined by the appended claims.

The invention claimed is:

1. A sampling and analysis device comprising:
a control unit for controlling the sampling and analysis device;
a tape wound on a tape reel carrying the tape, said tape comprising a base material with a series of reagent pads, the reagent pads arranged to provide a detectable response in the presence of at least one substance in the sample;
a tape mover, arranged to move and unwind the tape;
a dosing device arranged to provide a part of the sample onto one of the reagent pads; and
an optical sensor device arranged to detect optical radiation from said reagent pad supplied with said part of the sample, and to analyze the detected optical radiation to provide an indication of a presence or concentration of said at least one substance,
wherein the dosing device comprises:
a displaceable nozzle having an opening and a supply line for supplying a portion of the milk sample to the nozzle, the nozzle being adjacent to and below the reagent pads for supplying the part of the sample upwardly to the reagent pad, wherein the dosing device further comprises a nozzle mover arranged to move the displaceable nozzle towards and away from the tape, and an overflow device comprising a wall at least partly surrounding the nozzle, an overflow space being provided between the wall and the nozzle, and a discharge connected or connectable to the overflow space.

2. The sampling and analysis device according to claim 1, further comprising a dosing control device comprising a wall part for closing off the nozzle opening upon contact, and a mover arranged to position the wall part between the nozzle opening and the tape.

3. The sampling and analysis device according to claim 2, wherein the wall part is a flat wall part.

4. The sampling and analysis device according to claim 2, wherein the wall part comprises a flexible material.

5. The sampling and analysis device according to claim 2, further comprising a sealing rim arranged around the wall part, the sealing rim and the wall part together forming a second space for receiving the nozzle.

6. The sampling and analysis device according to claim 5, wherein, when the nozzle is received in the second space, the wall of the overflow device and the sealing rim are in sealing contact, the overflow space and the second space being in direct fluid connection.

7. The sampling and analysis device according to claim 1, wherein the wall at least partly surrounding the nozzle is a cup.

8. The sampling and analysis device according to claim 1, further comprising a dosing control device comprising a wall part for closing off the nozzle opening upon contact, and a mover arranged to position the wall part between the nozzle opening and the tape, to press the wall part and the nozzle onto one another.

9. The sampling and analysis device according to claim 8, wherein the wall part comprises an elastic membrane.

10. The sampling and analysis device according to claim 8, wherein the wall part comprises a flexible material.

11. The sampling and analysis device according to claim 3, comprising a sealing rim arranged around the wall part, the sealing rim and the wall part together forming a second space for receiving the nozzle.

12. The sampling and analysis device according to claim 4, comprising a sealing rim arranged around the wall part, the sealing rim and the wall part together forming a second space for receiving the nozzle.

* * * * *